United States Patent
McCann (10) Patent No.: US 11,707,384 B1
(45) Date of Patent: Jul. 25, 2023

(54) BILATERAL COMPRESSION DEVICE

(71) Applicant: John McCann, Sandy, UT (US)

(72) Inventor: John McCann, Sandy, UT (US)

( * ) Notice: Subject to any disclaimer, the term of this patent is extended or adjusted under 35 U.S.C. 154(b) by 210 days.

(21) Appl. No.: 17/000,037

(22) Filed: Aug. 21, 2020

Related U.S. Application Data (63) Continuation-in-part of application No. 15/496,830, filed on Apr. 25, 2017, now abandoned, which is a continuation of application No. 15/491,583, filed on Apr. 19, 2017, now abandoned.

(51) Int. Cl.
| | |
|---|---|
| *A61F 9/02* | (2006.01) |
| *A61F 13/12* | (2006.01) |
| *A61F 9/04* | (2006.01) |

(52) U.S. Cl.
CPC .............. *A61F 9/026* (2013.01); *A61F 9/04* (2013.01); *A61F 13/124* (2013.01)

(58) Field of Classification Search
CPC .. A61F 9/026; A61F 13/00038; A61F 13/124; A61F 9/04; A61F 9/029; A61F 9/045; A61F 9/02; A61F 13/00029; A61F 13/122; A61F 2007/0004; A61F 2007/023; A61F 2009/021; A61F 5/3707; A61F 9/00772; A61F 9/028; A61H 1/008
See application file for complete search history.

(56) References Cited

U.S. PATENT DOCUMENTS

2006/0157064 A1* 7/2006 Davison .................. A61F 9/029
128/858

* cited by examiner

*Primary Examiner* — Ophelia A Hawthorne
(74) *Attorney, Agent, or Firm* — Holland & Hart LLP (57) ABSTRACT

The present invention provides an improved bilateral compression device for post-operative surgical site, the bilateral compression device including a central cavity presented by an outerwall and a circumscribing sidewall, the central cavity in receipt of a post-operative pillow further comprising an outer membrane separated from an inner membrane for exerting a central compressive force and central indentation force deflection towards the post-operative surgical area which varies from a surrounding compression force.

10 Claims, 7 Drawing Sheets

BILATERAL COMPRESSION DEVICE

CROSS-REFERENCES TO RELATED APPLICATIONS

This application is a continuation in part of and claims the benefit of U.S. non-provisional patent application Ser. No. 15/496,830, which was filed on Apr. 25, 2017 which was a continuation of Ser. No. 15/491,583 filed on Apr. 19, 2017.

FIELD OF THE INVENTION

The present invention is broadly directed to post operative treatment devices and, more particularly, to an improved postoperative bilateral compression device with contoured surfaces to diminish bruising, and swelling after periocular procedures.

BACKGROUND OF THE INVENTION

Functional eyelid surgery is performed to improve vision and ocular comfort. When the upper eyelids droop this can obscure the superior visual field and when the lower eyelid flips away from the globe (ectropion) or towards the globe (entropion) it causes the eye to become red, watery, irritated and the vision to blur. Eyelid changes are more common in our aging population. It is also estimated that cosmetic eyelid surgery is the third most popular elective cosmetic procedure in the United States and it is anticipated that functional and cosmetic eyelid procedures will continue to grow in demand in the coming years based on an aging population and on the excellent treatment success rates. Other non-invasive periocular procedures such as laser treatments, radiofrequency treatments, ultrasonic treatments, and injections with Botox and filler injections have also become more popular in recent years.

As a result of the increased number of periocular procedures, many people will experience the typical post-operative problems of swelling, and bruising caused by leakage of blood and serous fluid from microscopic capillaries which are unavoidable cut during surgery or non-invasive procedures. Studies have shown the top concern of patients before and after undergoing periocular procedures is bruising and swelling. Bruising of the eyelids may contribute to poor lid globe apposition which may lead to blurred vision and cause additional delays in the patient recovery. Bruising and swelling is typically rate limiting to returning to work or to a normal social calendar after a periocular procedure.

The vast majority of periocular procedures are bilateral with the minority being performed on only one side. An ideal post operative device to reduce bruising and swelling should be easily used in the majority of cases which are bilateral as well as adaptable to the minority of cases which are unilateral. The eyelid splint described in U.S. Pat. No. 4,907,580 is a unilateral device and would not be appropriate for most bilateral eyelid procedures.

In typical post-treatment care, it is recommended to utilize the PRICE principals, namely to protect, rest, ice, compress and elevate around the affected areas to help that area heal. However, the facial anatomy associated with the periocular region presents unique difficulties which are affected by surrounding tissue, cartilage and bones which interfere with the PRICE techniques. In addition, maintaining compression and ice on the ophthalmic postoperative areas can create physical and psychological discomforts upon the treated patient and the time honored recommendation to apply ice to the eyelids has not actually proven effective in controlled studies.

Because of the large vascular network around the periocular region, this area is subject to swelling and bruising which increases after any procedure which damages the microscopic network of capillaries. It would therefore be beneficial to have a device for use during the postoperative process which helps reduce bruising and swelling of the eyelids and area surrounding the treatment area. The eyelids have a robust vascular supply and only a thin distensible layer of skin that is not effective in concealing bruising and this tissue is easily distensible encouraging swelling. For many years eyelid surgeons have recommended frequent ice compresses for the first few days after periocular treatment to minimize bruising. For many injuries to many areas of the body ice and cooling therapies are thought to help decrease blood loss, bruising, swelling, pain sensation and to speed the rate of recovery. In the only published controlled studies on the use of ice compresses after eyelid surgery, ice was found to be ineffective at decreasing bruising and swelling and to not have a clinically significant impact on postoperative pain. So the almost universally recommended method of reducing bruising and swelling and pain after eyelid procedures has not proven effective when put to a scientific test. This is probably because although ice cooling can cause some vasoconstriction which should reduce bruising and swelling it also has been shown in well controlled scientific studies to markedly increase bleeding time as it slows down how long it takes the blood to clot.

Compression is one of the physical methods recommended by the PRICE principles. However, the regional anatomy of the periocular region makes compression difficult and, in some situations, dangerous. There is a need for an improved compression device which includes a periocular patch with a precise adjustment mechanism to control the pressure applied to areas around the periocular region allowing the improved compression device to apply a minimum yet effective pressure over the eyelids. For example, the capillaries in human skin are part of a low-pressure system with pressures of less than 12 mm Hg typically present in healthy young adults. Application of external pressure to the skin which is greater than the pressure inside the microscopic capillaries may cause the capillaries to collapse and to cease to provide nourishment for the surrounding tissue. This phenomenon may lead to formation of pressure ulcers of the eyelids similar to the ulcers which occur on the sacrum and heals of those confined to bed and unable to roll about thus redirecting pressure to various parts of the skin. Similarly applying overly tight compressive dressings which exceed the capillary perfusion pressure may result in severe ischemic pain and necrosis and scarring of the underlying skin. This has been responded when overly tight dressings applied to the lower face or forehead after surgery Some prior attempts include devices which exert "no less than 23 mm Hg and no more than 40 mm Hg" of pressure to the overlying skin. This is 2-3 times the capillary perfusion pressure and this pressure may lead to necrosis of the skin and scarring. Some additional attempts at overcoming these pressure issues include use of devices which present a space or vaults over the eyelids which have limited ability to apply pressure to the eyelid area and therefore to help reduce bruising or swelling of the eyelids.

External pressure applied to the eyelid is transmitted to the eyeball in the form of an increase in intraocular pressure. The normal intraocular pressure is <20 mm Hg and increasing intraocular pressure substantially above this level by applying an external pressure may increase the intraocular pressure. Increased intraocular pressure can cause optic nerve damage and blindness. Therefore, there is a desire for a device which applies a controlled external pressure of less than 12 mm Hg to the eyeball and nearby skin.

One of the most feared complications of periocular treatments or injections given in the periocular region is hemorrhaging of an artery or arteriole behind the eye. The area behind the eye is a closed compartment called the orbit lined on all sides except the side covered by the eyelids by bones. The bony orbit can only expand toward the distensible eyelids in the case of an orbital hemorrhage to relieve pressure. The eye can move forward about 1.2 cm in this situation significantly increasing the volume of the orbit and decompressing the obit. However, if an artery within the orbital compartment begins to bleed during or after a procedure the pressure in the orbital compartment can exceed the perfusion pressure of the eye. If this lasts for even a few minutes, blindness may result. This is one of the leading causes of vision loss after periocular procedures and can happen even with an injection.

By way of example, a common maneuver performed in the emergency room in this situation is called inferior canthotomy and cantholysis which is an emergent minor surgical procedure performed at the patient's bedside to release the eyelid so the globe can move forward and decompress. Conversely, an external compression device which applies a pressure to the eyelids over the underlying eye can prevent the eye from moving forward during retrobulbar hemorrhage and thus prevents the orbit from decompressing. At the conclusion of a surgical procedures, a surgeon may tape on a pressure patch. If the pressure patch prevents the eye from moving forward or decompressing, a patient could lose vision from a retrobulbar hemorrhage.

Application of pressure to the bony orbital rim may help diminish the potential loss from a retrobulbar hemorrhage because it is not typically transmitted to the orbital compartment and therefore does not typically prevent the eye from moving forward. By providing a periocular compressive device that applies most of the compressive force peripherally over the orbital rim and less compressive force centrally over the eyelids. If one reviews FIGS. 1-3 of U.S. Pat. No. 4,907,580 it is evident from the shape of that device a significant amount of pressure would be applied to the central eyelid skin and this would likely contribute to a rise in orbital pressure and blindness in the case of a retrobulbar hemorrhage. Even in the absence of an orbital hemorrhage such a forceful central compression of 23-40 mm Hg would increase the intraocular pressure and could damage the optic nerve as is routinely observed in glaucoma. Use of this device for post procedure management of patients in some situations may be considered malpractice.

It would be beneficial to provide a post procedure compression device which allows for small adjustments to the compressive pressure to be less than the capillary perfusion pressure (approximately less than 12 mm Hg) and thus avoiding skin necrosis. It would also be beneficial to if the post procedure compression device applies less pressure over the eye than over the orbital rim so as to not transmit excessive pressure to the inside of the eye. Another desirable feature of a post procedure compression device would also allow for forward movement of the eye for decompression within the orbital space such as in the case of retrobulbar hemorrhage.

Too much pressure applied over the central eyelid can prevent forward eye movement such as in the case of retrobulbar hemorrhage. A measure of how much pressure must be applied to indent an object is the indentation force deflection (IFD). A high indentation force deflection means that it takes a lot of pressure to compress an object a little as is the case with a very firm pillow. A high IFD device applied over the central eyelid skin would prevent the eye from easily moving forward in the case of a retrobulbar hemorrhage. Thus, it would be desirable to provide a post procedure compressive device with a low IFD presented along the periocular region to allow forward eye movement for decompression in the case of an orbital hemorrhage.

In the past, one solution has been to apply compressive eye patches post-operatively to the post-operative surgical area, e.g. the periocular area, with adhesive tape to help with recovery. However, eye patches are not acceptable for cases when both eyes are undergoing recovery for an extended period of time because they temporarily blind the patient and this can create additional anxiety issues and physical limitations for the patient during the recovery process. Releasing patients to home after periocular treatments with taped-on compressive dressings over both eyes may result in greater risk of falls and other injuries. This complication can be avoided with a post procedure compressive device which is worn while the patient is seated or supine but which is easily removed allowing vision when the patient walks about. It is also difficult to adjust the precise tension such a patch applies to the skin. In addition, a taped-on patch generally has little flexibility, presenting a high IDL and thus does not readily allow the eye to move forward in the case of retrobulbar hemorrhage.

Accordingly, there is a need for an improved post procedure periocular device which safely applies a pressure of less than 12 mm Hg to the periocular skin, applies minimal yet effective pressure to the eyelid skin overlying the globe, has a low IFD in the areas which contacts the skin overlying the globe, is removable so the patient can see to walk about, but when in place providing desired bilateral or unilateral compression as needed to assist the patient during the recovery period and addresses at least a portion of the aforementioned shortcomings.

SUMMARY OF THE INVENTION

The present invention includes an improved bilateral compression device for post-treatment care of the periocular region. The bilateral compression device including a central cavity presented by an outerwall and a circumscribing sidewall, said central cavity in receipt of a postoperative pillow further comprising an outer membrane separated from an inner membrane for exerting a central compressive force towards the post-operative surgical area which varies from a surrounding compression force. The central compressive force is less than the surrounding compressive force and the portion of the device creating the central compressive force is of low IDL. The device also provides cooling and comfort by adjusting to the contour of the wearer and allowing for easy removal and precise adjustments to the applied compression around the periocular area.

Various objects and advantages of the present invention will become apparent from the following description taken in conjunction with the accompanying drawings wherein are set forth, by way of illustration and example, certain embodiments of this invention. The drawings submitted herewith constitute a part of this specification, include exemplary embodiments of the present invention, and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 10 generally refers to an embodiment of the present invention, a bilateral compression device designed to be worn on the head of the patient after periocular procedures to assist in the healing process. The bilateral compression device 10 includes a central cavity 20 presented by an outerwall 18 and a circumscribing sidewall 12 which generally extends along the outerwall 18.

Example materials which may be used for the outerwall 18 and circumscribing sidewall 12 include but are not limited to plastics and metals. In one embodiment, the outerwall 18 and circumscribing sidewall 12 may comprise a single rigid piece for example using an injection molding process. In one exemplary embodiment, the bilateral compression device 10 may utilize a goggle like one commercially available from Smith Optics, Inc. In yet another exemplary embodiment, the outerwall 18 and circumscribing sidewall 12 may be made from different rigid materials, each having different properties and different shapes as desired.

The circumscribing sidewall 12 generally extends from the outerwall 18 providing a rim and in one embodiment may present a pair of slotted openings 14 which generally receive an elastic band 16, also referred to as a headband, for easy removal and adjustment of the bilateral compression device 10. In one embodiment, the outerwall 18 and sidewall 12 are rigid structures to direct the applied force along the bony orbital rim and surrounding structure, avoiding the upper and lower eyelid which overlies the eye. In one embodiment, the outerwall 18 and sidewall 12 are sufficiently dimensioned to apply pressure along the portions of the face typically impacted by bruising after periocular procedures. By way of example, the outerwall 18 and sidewall 12 may extend 2 cm above the superior orbital rim, 2 cm lateral to the orbital rim, 3 cm below the orbital rim and medially over the base of the nose. Alternatively, the headband 16 may be attached to clips inserted through circumscribing sidewall 12. The elastic band 16 also allows the bilateral compression device 10 to remain on during the night while the patent sleeps. Generally, the elastic band 16 is provided that generally includes an elastic or resilient material to allow stretching of the elastic band 16 as desired for placement or removal of the bilateral compression device 10. Generally, the elastic band 16 with the outerwall 18 and circumscribing sidewall 12 use a micro-adjustment mechanism 40 to present a biased contoured surface for applying a precisely titrated pressure to a periocular region or post operative region which for a typical user may include the eyelids and the area peripheral to the eyelids. The biased countered surface includes a compressive surface which can extend around the area associated with the eyelids, base of the nose and orbital rim, extending at least 2-3 cm peripheral to the orbital rim (not shown).

In some cases, the elastic band 16 may slide upward or downward on the back of the head which may result in elongation of the elastic band 16 and thus alter the pressure applied to the post operative surgical site associated with the bilateral compression device 10.

Figure 1:
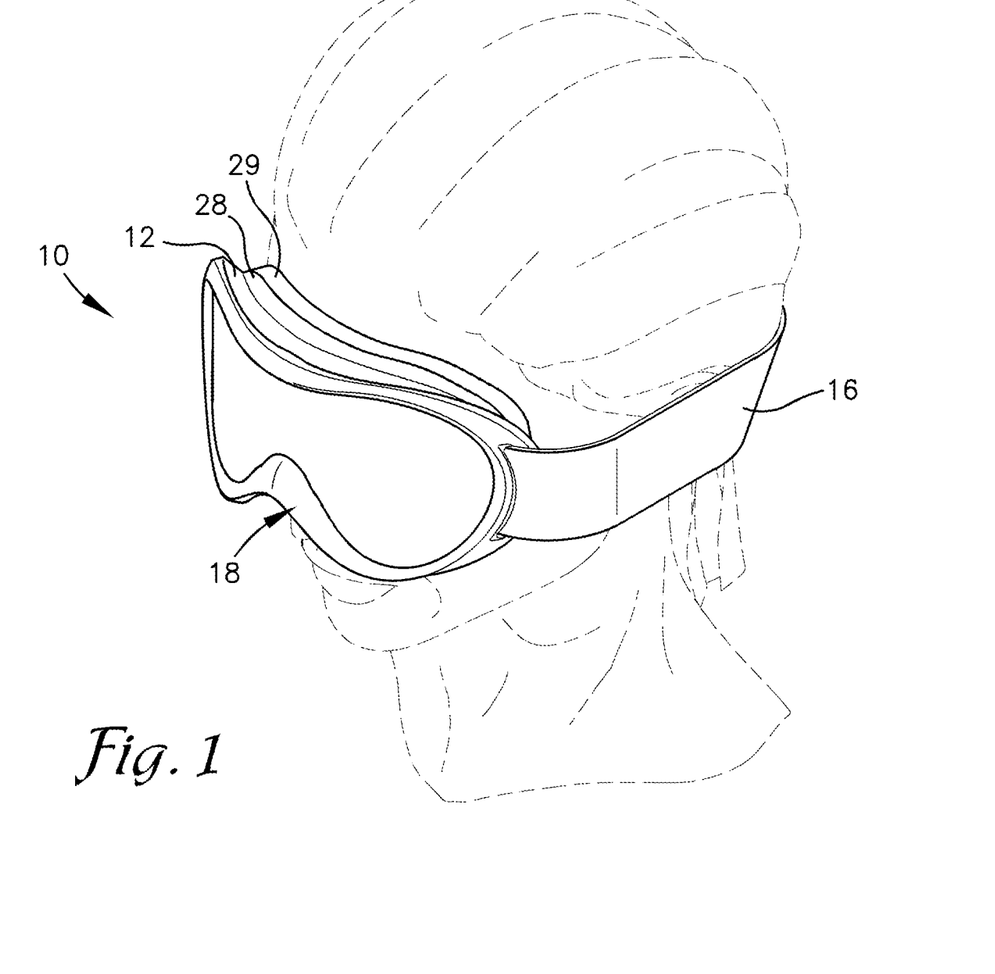
FIG. 1 is a left side perspective view of an exemplary embodiment of bilateral compression device.

The bilateral compression device 10 generally outlines the periocular region associated with the post-treatment surgical area with the circumscribing sidewall 12 extending along the outer area of the post-treatment surgical area. In the depicted embodiment of FIG. 1, the circumscribing sidewall 12 extends along the outerwall 18 and presents a contact surface which extends around the optical socket and nose bridge area and may include a straight line, arc, polygon or irregular shape for extending along the post-operative surgical area.

The micro adjustment mechanism 40 allows the tension in the elastic band 16 to be positionally adjusted in a way which is easily reproducible and measurable to carefully titrate the compressive forces exerted by the bilateral compression device 10. Numbered indices of regular intervals may be printed along the band 16 allowing for adjustment of the strap to a desired compressive force which does not exceed the capillary perfusion pressure. A nomogram may be used which allows measurable and easily repeatable adjustment of the band 16 to provide the desired compression based, for example, on the wearer's head-diameter. The micro-adjustment mechanism 40 provides an easily measurable band which assist in providing a safe and effective compression of the periocular region.

In one embodiment, the nomogram may include a least one set of indicia positioned along the band 16 with a position indicator 102 configured for receiving the band 16 with the indicia 42 spaced there along. By way of example, the set of indicia 42 may correspond to the head circumference or correspond to the magnitude of applied compression. The nomogram may also include various visual elements including color or graphic elements to indicate that the compression settings are within a safe range versus an unsafe range or a desired range versus an undesired range. The micro-adjustment mechanism 40 helps provide a safe and effective compression of the post procedure compression device.

Generally, the central cavity 20 extends inferiorly from the outerwall 18 outwardly along the circumscribing sidewall 12 and is adapted for receipt of a plurality of membranes. Alternatively, the central cavity 20 could include an area, at least partially extended exteriorly through the outerwall 18.

Figure 2:
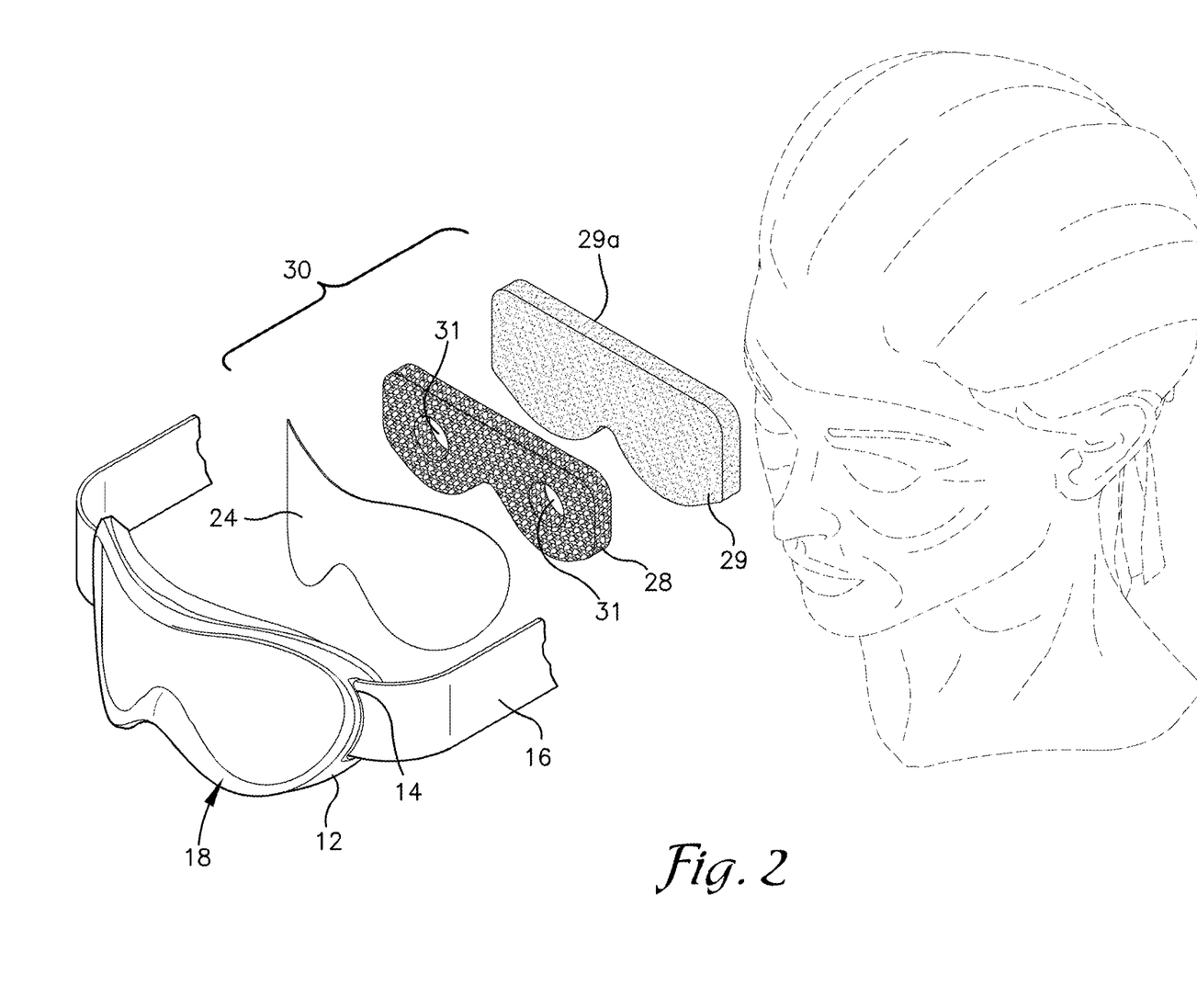
FIG. 2 is an exploded side perspective of the exemplary embodiment of FIG. 1.
Figure 3:
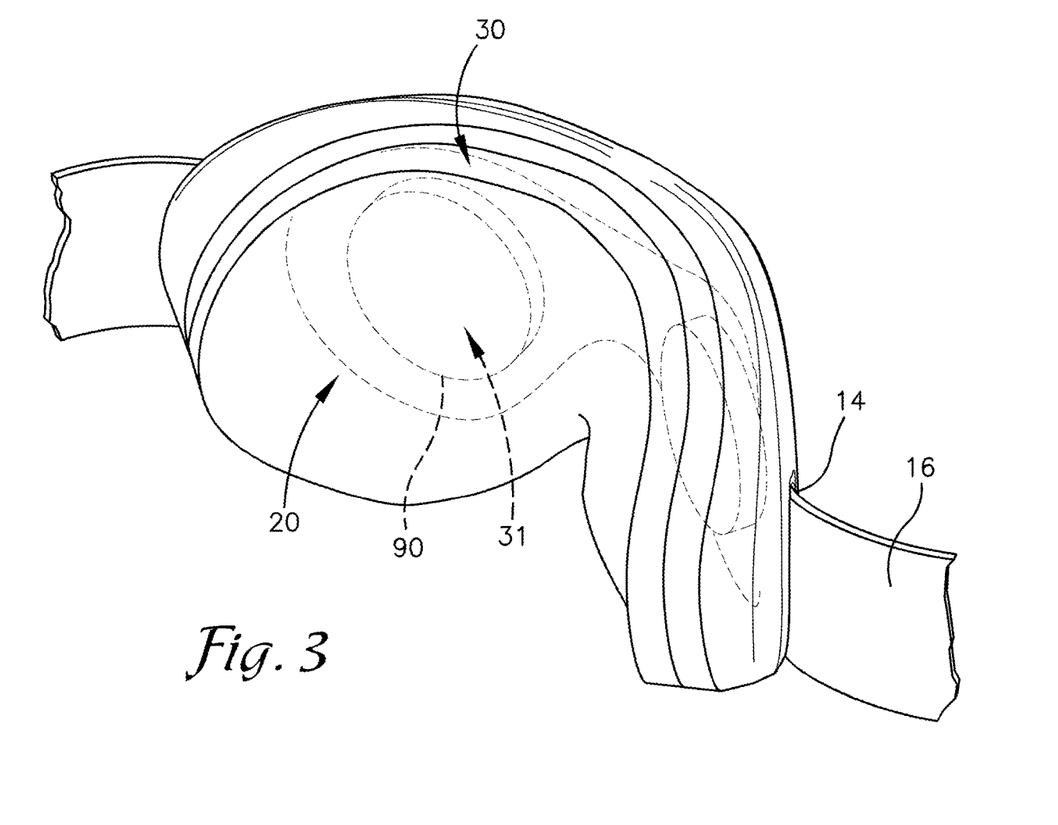
FIG. 3 is a rear perspective of the exemplary embodiment of FIG. 1.

An exemplary embodiment of a post-operative pillow 30 is depicted in FIG. 2 and includes an outer membrane 24 separated from an inner membrane 29 by an IFD reducing membrane 28. The IFD reducing membrane provides a prolapse receiver for receiving the inner membrane 29 a depth of 1.2 cm or more in the event of a retrobulbar hemorrhage to allow for forward movement of the eye. Generally, the recess 31 presents a pair of shaped passages presenting a passage in which either one or both eyes can prolapse into in the event of a retrobulbar hemorrhage. In one embodiment of the bilateral compression device 20 the inner membrane 29 has plural perforations 90 centrally located along the central portion of the inner membrane allowing for removal of the central portion such that when they are removed the void created in the inner membrane 89 lines up with the recess present in the IFD reducing membrane 28. Once the central portion is removed from the inner membrane, the light may enter through the central portion allowing for visual communication therethrough. In some situations, it may be beneficial to remove the central portion or only one side of the central portion, where for example, it is desirable to apply pressure to one eye after a unilateral treatment while allowing vision through the other eye.

Generally, the post-operative pillow 30 is configured for receipt by the central cavity 20. In operation, the post-operative pillow 30 provides multiple compressive forces upon the post-operative surgical area. In the depicted embodiment of FIG. 2, the post-operative pillow 30 provides a reduced compressive force along a central area 31 within said IFD reducing membrane 28 having a left and right side, also referred to as a pair of recesses. In addition to a reduced central compressive force the recess in the IFD reducing membrane reduces the central IFD. Generally, the IFD reducing membrane 28 has a greater compressive force extended outwardly from the opening associated with the recess 31 towards the facial area surrounding the post-operative surgical area, less force and lower IFD being applied along the recess 31 associated with the delicate facial area such as the area associated with the wearer's eyelid and globe tissue. While the embodiment depicted in FIG. 2 generally provides for a bilateral compression, or two different compression forces and different IFD's, additional compression forces and IFD's may be utilized in the present invention as desired for selectively safely reducing the swelling and discomfort associated with the post-operative surgical area to assist in the healing process.

The compression forces exerted upon the post-operative surgical area by the bilateral compression device 10 generally correspond to the properties of the post-operative pillow 30. Generally, two compression forces and IFD's are provided, a central compression force with low IFD and a surrounding greater compression force. The central compression force corresponds to the recess 31, while the surrounding compressive force corresponds to the IFD reducing membrane 28. Thus, the compression forces and IFD exerted upon the post-operative surgical area vary by the configured recess 31 and the selected IFD reducing membrane 28. Generally, the desired compression for the central compression force is less than the pressure from the surrounding compression force. The recess 31 is configured to reduce the central compression force and decrease the IFD thus limiting resistance should the globe need to move forward to decompress the orbital compartment in the case of postoperative orbital hemorrhage.

The outer membrane 24 is generally an opaque or translucent rigid material which is configured for placement between the outerwall 18 and the central cavity 20. The outer membrane 24 may also provide a moisture barrier to prevent any unwanted condensation within the central cavity 20 during use. The outer membrane 24 depicted in FIG. 2, generally has a continuous layer which is adapted for placement on the outerwall 18 along the inner cavity 20 and for receiving the IFD reducing membrane 28. The outer membrane 24 may be secured with, for example, an additional adhesive layer (not shown) to the IFD reducing membrane 28. The adhesive layer may also be omitted, or otherwise modified as is known for securing the outer membrane 24 to the IFD reducing membrane 28.

The post-operative pillow 30 is configured for receipt within the central cavity 20 and generally provides for compression along the relevant facial contours such as the nose bridge, eyelid and/or eye-socket as well as 2-3 cm peripheral to the bony orbital rim (not shown). In the depicted embodiment of FIG. 2, the post-operative pillow 30 generally includes the inner membrane 29 and the IFD reducing membrane 28. One embodiment of the IFD reducing membrane 28 includes utilization of a generally compressible cellular material which is compressible, moisture resistant and provides thermal insulation. The compressible cellular material associated with the IFD reducing membrane 28, when utilized, of FIG. 2 may be used either individually or in combination with different or additional material and either configured as a continuous layer or selectively positioned within the central cavity 20 to provide the desired protection and compressibility at the relevant post-operative location. By way of example, the material used for the IFD reducing membrane 28 may be, but is not limited to, a laminated cellular foam material which is moisture resistant and has a thickness of at least 1.2 cm thick. An example of commercially available material includes ENSOLITE styles IV1, IV2, IV3, IV4, IV5, GIC OR IVC all manufactured by Ensolite, Inc. of Mishawaka, Ind.

The IFD reducing membrane 28, is configured for placement within the circumscribing sidewall 12 for receipt by the central cavity 20. Generally, the IFD reducing membrane 28 may be bonded directly to the outerwall 18 to help keep out moisture and maintain the interior temperature within the central cavity 20 during use.

The inner or facial membrane 29 is generally fabricated from a material designed to cushion the treated area of the patient body after the surgical procedure. It will be at least ¾" thick allowing it to mold to the contours of the periocular region. During use, the facial membrane 29 may become dirty or soiled from use in connection with the post-treatment use. In one embodiment the pressure applied by the inner facial membrane 29 will be utilized to hold sterile disposable eye pads in place by friction. The facial membrane 29 in the depicted embodiment, is substantially planar with a configuration which generally corresponds to the central cavity 20. The inner membrane 29 may be fabricated from a variety of compressible materials which are suitable for treating wounds but in a preferred situation, it would have a smooth, comfortable surface which would limit irritation or adhesion to the post-operative area. By way of example, and not as a limitation, the inner membrane 29 may be fabricated from a compressible polyurethane foam material with a coating. Generally, the inner membrane 29 is breathable, flexible with a durable coating having excellent properties which prevent it from adhering to the recently treated area. In addition, it may include a phase-change water-based coating which may help it maintain an ideal comfortable temperature by acting as a heatsink, and conducting heat away from the surface. Examples may include material made by Mentor Corporation under the trade name EPIFOAM or TOPIFOAM. Another example may include material made by Bergad Specialty Foam under the trade name COOLCELL.

In one embodiment, the inner membrane 29 may also include an inner coating 29a which is non-absorbent and easily washed to limit absorption by the inner membrane 29 of ointments used after treatment or blood from absorbing into the material. By way of example, and not as a limitation, the inner coating 29a may include vinyl which is water repellant, easily washed, non-adhesive, and hypoallergenic.

The inner membrane 29 may be secured to the IFD reducing membrane 28 or to the circumscribing sidewall 12 mechanically with, for example, silk, thread or chemically with for example adhesive. The central portion of the inner membrane 29 may be removed and frictionally secured to the remainder of the surrounding inner membrane 29 to allow for visual communication through the central cavity 20, for example, to allow the patient to see through the compressive pillow on the side or sides where a portion of the inner membrane 29 has been removed.

In another embodiment, the inner membrane 29 may be fabricated from foam with a covering on the side of the foam that touches the skin composed of a gel, graphite or a vinyl mixture or some other material to allow heat to be carried away from the skin and/or to be cooled. It may be fabricated from a type of foam that has cooling properties or properties of being non-absorbent, hypoallergenic, and easily cleaned independent of any coating.

In one operational embodiment, the circumference of the patient's head will be measured immediately before the bilateral compressive device 10 is applied using a flexible disposable tape measure. The fastening mechanism 40 may include one or more position indicators 102 with window for receiving the band 16 with the spaced and numbered indices 42.

Figure 7:
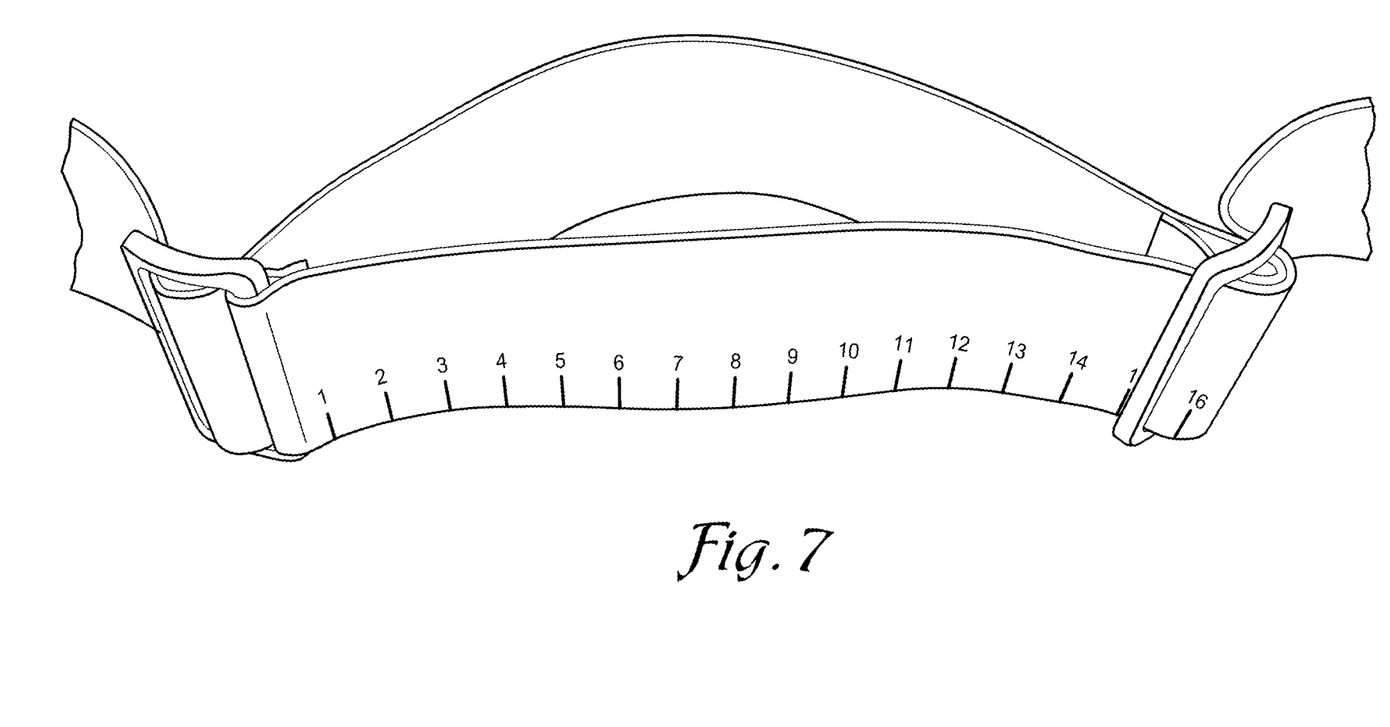
FIG. 7 is a rear perspective view of an alternative embodiment of a nonogram illustrated along a portion of the headband with spaced indicia.

As illustrated in FIG. 7 a nomogram may be utilized on the headband 16 with a plurality of indices 42 spaced along the headband 16 with an adjustable position indicator 102 which indicates the current position and allows for adjustment of the headband 16. Generally, the headband 16 is adjusted to provide the desired compression. Adjustment to the desired numerical index 42 is based on the head circumference and the length of the band 16. The selective adjustment allows for precise titration of the compressive force applied by the bilateral compression device 10 to the user. The fastening mechanism 40 allows for easy removal of the bilateral compressive device 10 to facilitate vision when the patient is ambulatory or to facilitate application of ointments or drops and the changing of the disposable sterile dressing secured by the bilateral compressive device 10.

Figure 4:
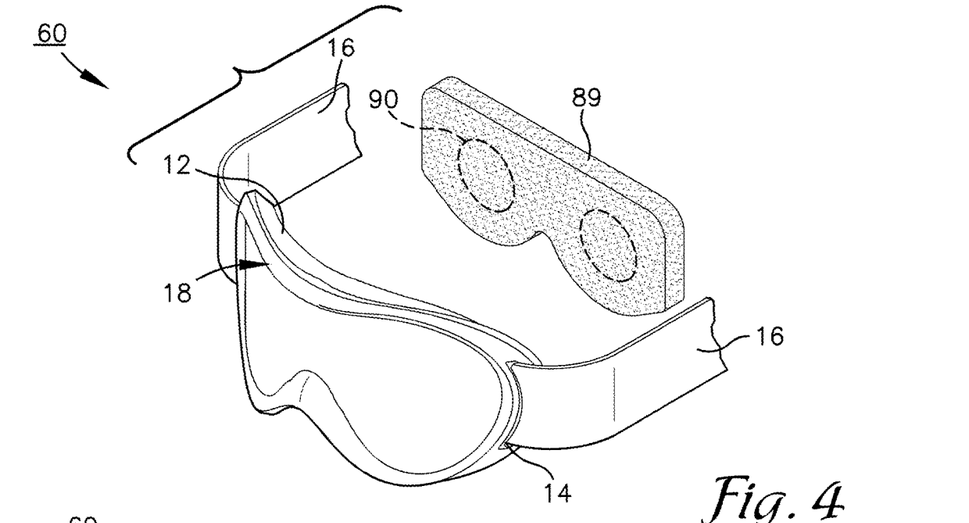
FIG. 4 is a side perspective of an alternative embodiment of the bilateral compression device.
Figure 5:
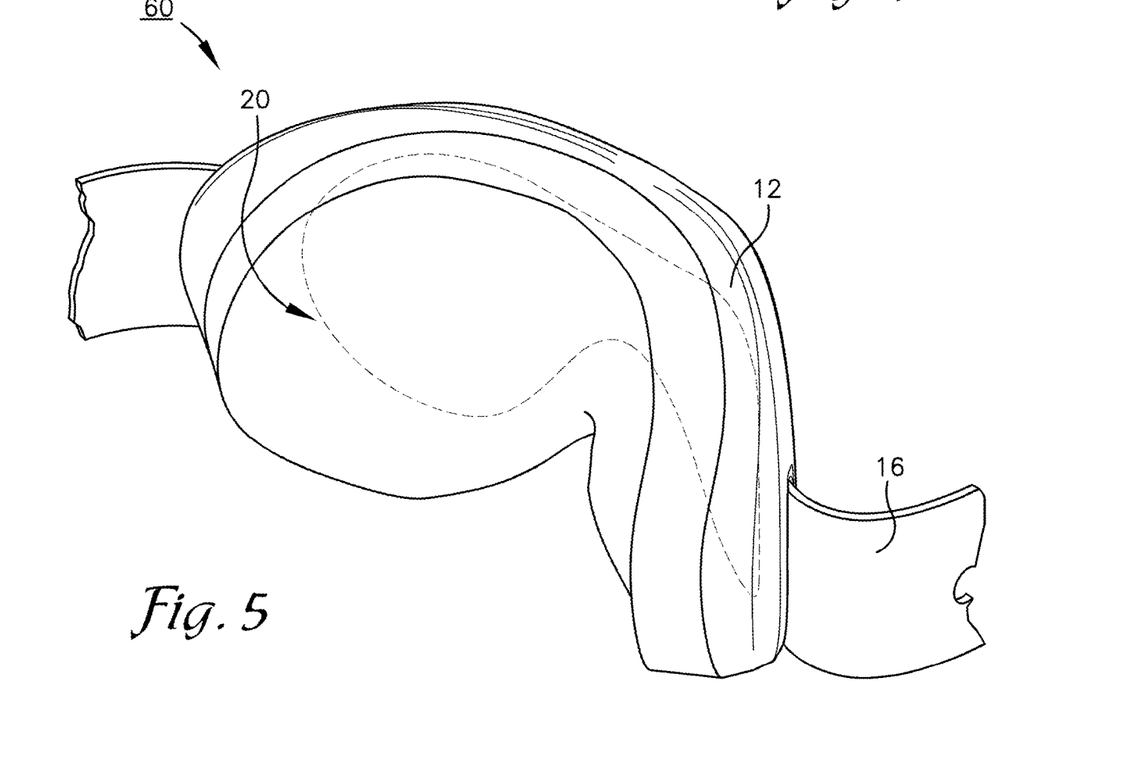
FIG. 5 is a rear perspective of the alternative embodiment of FIG. 4.

An alternative embodiment of the bilateral compression device 60 is illustrated in FIGS. 4-5 with central cavity 20 adapted for receipt of an alternative inner membrane 89 having optional perforations 90 for selective removal of a portion thereof for visual communication through the inner membrane 89. For example, the central portion associated with each of the left and right side of the inner membrane 89 may each be irregularly shaped or regularly shaped as presented by the plural perforations 90 spaced along the inner membrane 89 for selective removal of one or both of the left or right side central portion associated with the recesses 31 to allow for visual communication therethrough. In this way, the central pressure for at least one side may be reduced and the wearer may be able to see through the inner membrane 89, and the IFD reducing membrane 28 and outer membrane 24 allowing the patient to walk about with the compressive device in place while simultaneously avoiding various injuries.

Figure 6:
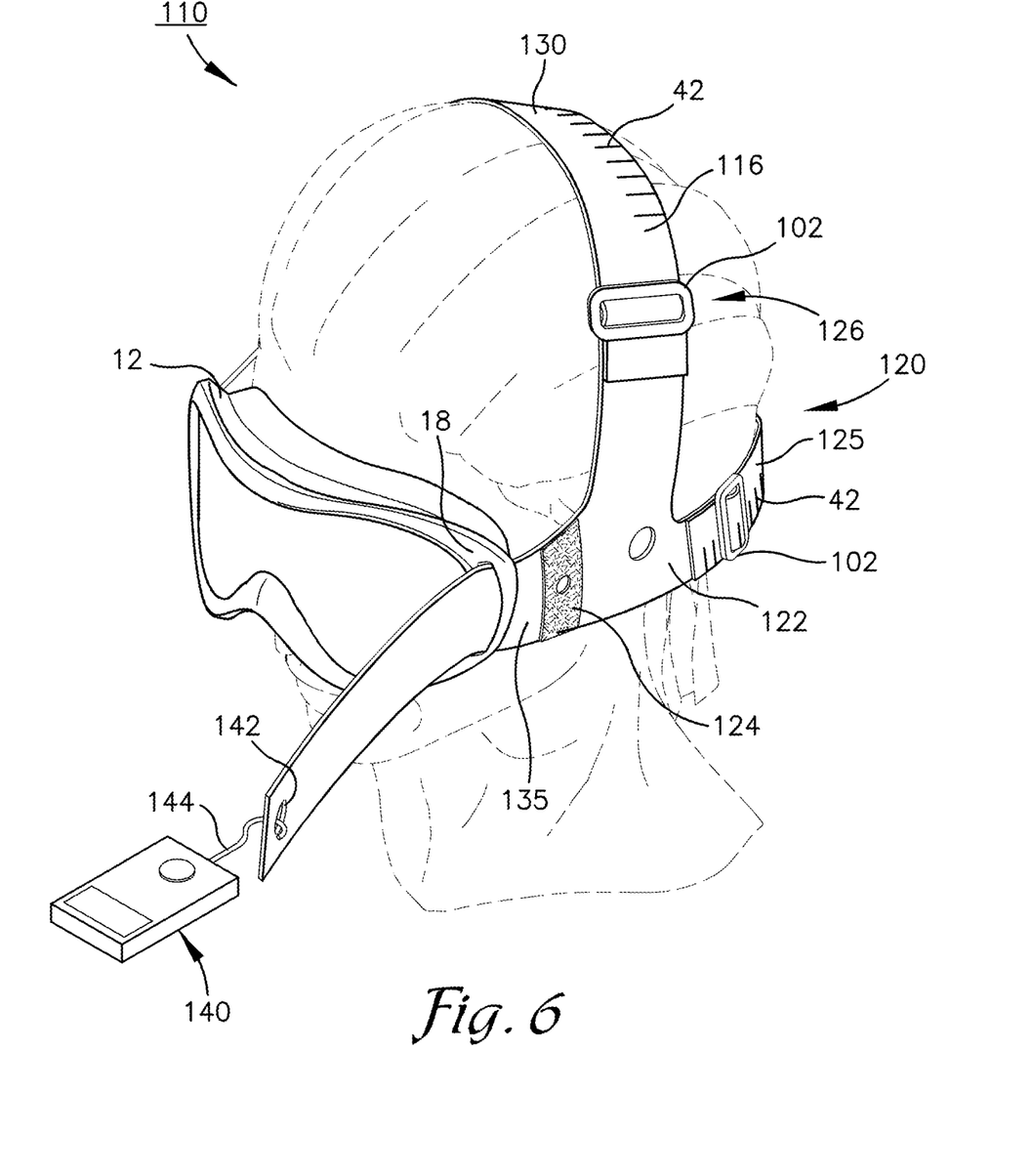
FIG. 6 is a side perspective of a second alternative embodiment of the bilateral compression device.

In another alternative embodiment of the bilateral compression device 110 illustrated in FIG. 6, a shaped headband 116 is provided which includes a superior support 130 which is designed to limit unwanted downward movement of the inferior portion 125 of the band 16 during wear. Generally, the illustrated shaped headband 116 includes the position indicator 102, an inferior portion 125, a superior portion 130 and an anterior projection 135 joined at a headband junction 122.

During wear, the inferior portion 125 extends rearwardly from the headband junction 122 to rest on the inferior edge of the occipital protuberance of the wearer's head. The inferior portion 125 generally provides posterior and downward bias for the bilateral compression device 110 which is at least partially offset by the superior portion 130 to stabilize the bilateral compression device 110 so that downward movement on the back of the head is limited.

The superior portion 130 extends from the headband junction 122 vertically towards a vertex of the skull and provides vertical bias which at least partially vertically supports the bilateral compression device 110. The bias presented by the superior portion 130 at least partially offsets the downward bias presented by the inferior portion 125. The superior portion 130 and inferior portion 125 are joined to present a posterior opening 126 which when worn, encircles a portion of the occipital and parietal bone associated with the wearer's head.

The anterior projection 135 extends from the bilateral compression device 110 towards the headband junction 122 and is generally configured for receipt by slotted openings 14. The distal or anterior projection 135 attaches posteriorly to the headband junction 122 where the anterior, inferior and superior portions 135, 125, 130 intersect. The proximate posterior end of the anterior projection 135 is located opposite the headband junction 122 and near the bilateral compression device 110. In one embodiment, the anterior projection 135 is aligned with the slotted openings 14 using for example a fastener 124 such as a hook and loop fastener, which is easily adjusted during the initial configuration of the bilateral compression device 110 for wear by a user. By aligning the anterior projection 135 with the slotted openings 14, the tension on the anterior projection 135 can be easily adjusted and readily secured as desired for applying the selected compression upon the post operative surgical site. In one embodiment, the compression can be adjusted to a specific level using a compression measurement device or tool 140. In another embodiment, the compression can be adjusted by extending the anterior projection 135 to specific indicia 42 based on head diameter as further described below.

As illustrated in FIG. 6, an optional compression measurement tool 140 may be utilized to configure the alternative bilateral compression device 110, the compression force being measured with, for example, a scale. The embodiment of the fastener 124 associated with the anterior projection 135 includes a readily adjustable hook and loop type fastener 124. In addition, a receiver 142 is located on the proximate end of the anterior projection 135 which is adapted for connected operation by the compression measurement tool 140. The receiver 142 may alternatively be associated with the outerwall 18 or sidewall 12.

The compression measurement tool 140 may be digital or mechanical. The illustrated compression measurement tool 140 also includes attaching means 144, like a hook or other fastening structures which can be easily secured to and removed from the receiver 142. In operation, the compression measurement tool 140 includes internal force measuring structure connected to a visual display which indicates an increase or decrease in compressive force through a mechanical connection to the anterior projection 135.

Alternatively, the proximate end of the anterior projection 135 may include a plurality of numbered indicia 42 spaced along the anterior projection where each successive indicia 42 represents an increase in compression according to the well known Hooke's Law, where the end of the anterior projection is stretched or extended from an uncompressed position to the desired compressed position which will be customized to the patient's head diameter, the successive indicia 42 on the anterior projection 135 representing the extension directly corresponding to the applied compressive force according to F=k×e. The numbered indicia 42 may be incremented to accommodate configuration of the bilateral compression device 110 for compression with users having varying head dimensions.

Figure 8:
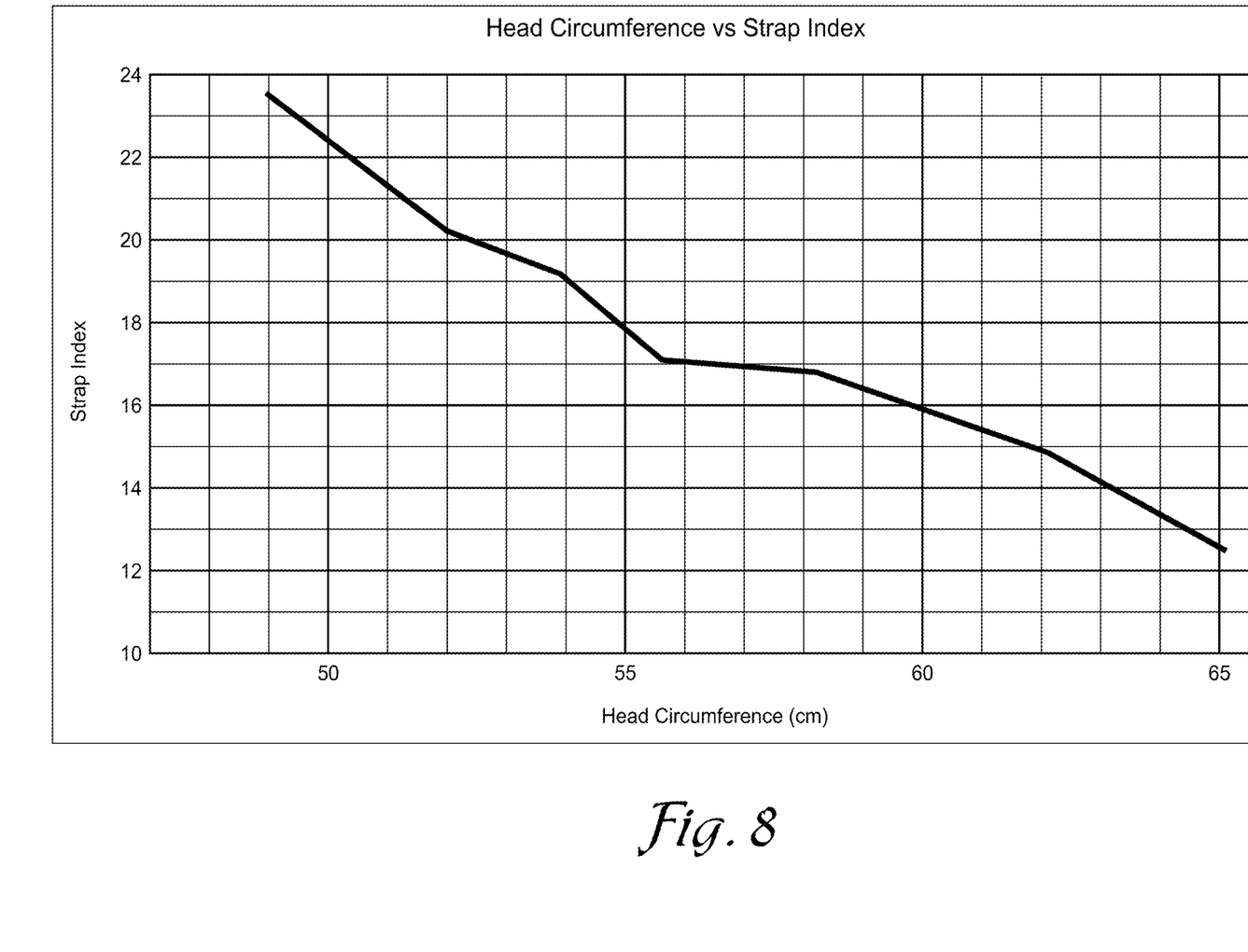
FIG. 8 is a chart illustration of the nonogram reflecting the exerted compression as a relationship between the head circumference and the numerical indicia illustrated on the headband.

For different types of materials there may be different amounts of compression. FIG. 8 shows a representative graph of different pressures as applied by the headband 16 to different head circumferences based on the selected numerical indicia 42. In operation, the user can titrate the exhibited compression by select the numerical index 42 which corresponds to the desired compression and circumference of the portion of the user's head which is receiving the portion of the headband 16. In one example, the nonogram may be utilized in connection with one or more of the anterior, inferior and/or superior portions 135, 125, 130 providing a quick and easy way to adjust the compressive characteristics of the bilateral compressive device 110.

Alternatively, plural pressure sensors (not shown) may be embedded within or along a surface of the alternative facial membrane 89 for aligning the tension on the shaped headband 116 to a desired pressure. The pressure sensors (not shown) may utilize wireless or wired communication technologies, including Bluetooth, for conveying the associated tension data as determined by the pressure sensor (not shown) at a location using for example a microprocessor. The conveyed data may be displayed graphically or numerically on a user device, such as a smartphone, and may include an over-limit or under-limit alarm or setting.

In an exemplary operation of the use of the compressive measurement tool 140, the anterior projection 135 is received by the slotted openings 14 and pulled forward. The compression measurement tool 140 is attached through the receiver 142 located on the proximate end of the anterior projection 135. The anterior projection 135 is then adjusted until the desired amount of compression is applied as indicated by the compression measurement tool 140 and then the anterior projection 135 is then secured to the shaped headband 116 to maintain the desired compression.

The anterior projection 135 upon the post-operative surgical site by the bilateral compression device 110 for proper adjustment of the tension applied to the bilateral compression device 10, 110 by the headband 16, 116.

Position indicator 102 may be located on, near or between any of the anterior, inferior or superior portions 135, 125, 130 to allow for measurably adjustment of the shaped headband 116 based in part on the desired compression and the variable shaped receiver with desirable comfort to accommodate various dimensions. The shaped headband 116 may include a plurality of position indicators 102 any one of which may be associated with one or more of the anterior, inferior or superior portions 135, 125, 130. Generally, the position indicator 102 includes a pair of upright members presenting a window for receipt of the band 16 and which helps with measurably adjusting the desired compression and upward and outward bias exerted by or upon the bilateral compression device 110.

Position indicators 102 may include length adjustment structures generally known, which may include, but is not limited to, various mechanical fasteners such as buckles, buttons and hook and loop fasteners. In addition, to adjustment of the bias, the length of at least one of the anterior, inferior 135, 125 may be adjusted as desired to titrate the compression force the device 110 delivers, using for example buckle, hook and loop or other type of length adjustment structure as desired for the position indicator 102.

The anterior projection, inferior and superior portions 135, 125, 130 may independently or collectively be fabricated from an elastic or flexible material which is adjustable and presents the desired bias to the bilateral compression device 110 for adjusting the pressure exerted upon a periocular region associated with the post-operative surgical area.

It is to be understood that while certain forms of the present invention have been illustrated and described herein, it is not to be limited to the specific forms or arrangement of parts described and shown.

What is claimed and desired to be secured by Letters Patent:

1. A postoperative bilateral compression device comprising:
   a central cavity presented by an outerwall and a circumscribing sidewall,
   said circumscribing sidewall presenting a contoured surface which extends along a curved planar surface;
   an adjustable band secured to said circumscribing sidewall for securing said post-treatment bilateral compression device;
   a post-operative pillow received by said central cavity;
   said postoperative pillow further comprising:
   an outer membrane;
   an inner membrane positioned adjacent to said outer membrane;
   an indentation force deflection (IFD) reducing membrane separating said outer membrane and said inner membrane; wherein said IFD reducing membrane is configured to present a surrounding compression force directed towards a post-treatment surgical site.

2. The post-operative bilateral compression device of claim 1 wherein said inner membrane further comprises a left side and a right side wherein at least some of one of said left and right side is removable.

3. The post-operative bilateral compression device of claim 1 wherein said inner membrane presents a smooth, non-absorbent, non-stick surface.

4. The post-operative bilateral compression device of claim 1 wherein said inner membrane has a coating.

5. The post-operative bilateral compression device of claim 1 wherein said post-operative pillow provides a reduced centrally compressive force with a low IFD.

6. The post-operative bilateral compression device of claim 1 wherein said circumscribing sidewall is configured to present a sealing surface which extends along the post-treatment surgical site.

7. The post-operative bilateral compression device of claim 1 wherein said outer membrane provides visibility through said postoperative bilateral compression device.

8. The post-operative bilateral compression device of claim 1 wherein said band further comprises a plurality of indicia for adjustment of said centrally compressive force.

9. The post-operative bilateral compression device of claim 1 further comprising a plurality of pressure sensors embedded in said postoperative pillow for quantitative adjustment of said central compressive force.

10. The post-operative bilateral compression device of claim 1 wherein said band includes a receiver for receipt of a compression measurement tool for quantitative adjustment of said central compressive force.

* * * * *